United States Patent
Ahmad et al.

[11] Patent Number: 5,925,048
[45] Date of Patent: Jul. 20, 1999

[54] BONE SCREW

[75] Inventors: Shaher Ahmad, Dallas; James D. Lafferty, Colleyville; Rick A. Buss, University Park; Brian A. Buss, Dallas, all of Tex.

[73] Assignee: Osteomed, Dallas, Tex.

[21] Appl. No.: 09/042,229

[22] Filed: Mar. 13, 1998

[51] Int. Cl.⁶ .................................................. A61B 17/86
[52] U.S. Cl. ........................................................ 606/73
[58] Field of Search ................................ 606/73, 72, 65, 606/66, 104; 411/404, 411, 417

[56] References Cited

U.S. PATENT DOCUMENTS

| | | | |
|---|---|---|---|
| 3,236,141 | 2/1966 | Smith | 606/73 |
| 5,098,434 | 3/1992 | Serbousek | 606/73 |
| 5,372,598 | 12/1994 | Luhr et al. | 606/69 |
| 5,470,334 | 11/1995 | Ross et al. | 606/72 |
| 5,486,176 | 1/1996 | Hildebrand et al. | 606/71 |
| 5,601,553 | 2/1997 | Trebing et al. | 606/61 |

Primary Examiner—Guy V. Tucker
Attorney, Agent, or Firm—Richard K. Thomson

[57] ABSTRACT

A self-drilling, self-tapping screw for use in repairing broken bones. The screw is made of a high strength material selected from the group consisting of titanium alloys, chrome cobalt, and high strength resinous polymer. The screw has threw segments: a tip region, a body region and a head region. The tip and body regions have a retention thread formed over substantially their entire lengths. The tip has an included angle α in the range between 45° and 50°. The head region is specifically designed to maximize the torque it can withstand and minimize the amount of material removed in formation of the recess. The head has a generally frusto-conical shape with an included angle of between 90° and 120° to prevent pull through while minimizing the head's profile. The retention threads on the tip region and the body region have similar shapes and pitches with the pitch on the tip region being slightly smaller than the pitch on the body region. Each of the retention threads has a lead angle between 48° and 52°, and a trailing angle between 98° and 102°, as measured from the centerline of the screw.

14 Claims, 1 Drawing Sheet

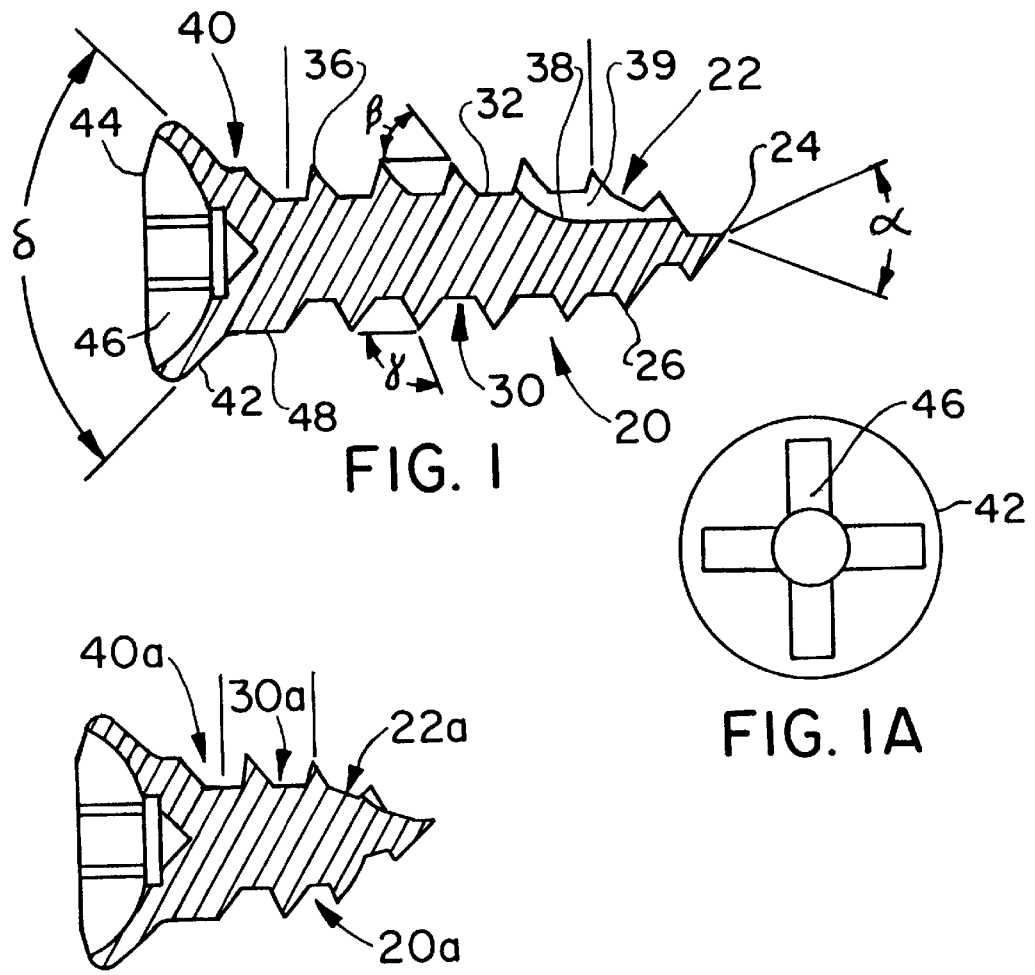
FIG. 1
FIG. 1A
FIG. 2
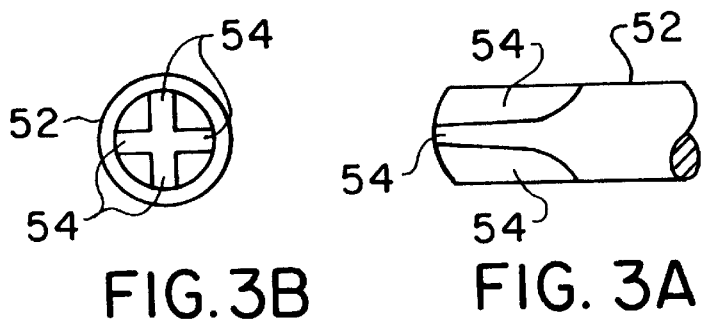
FIG. 3B
FIG. 3A
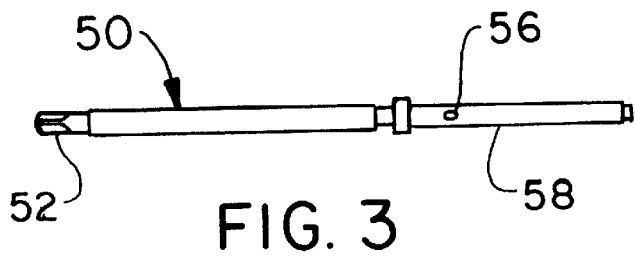
FIG. 3

BONE SCREW

The present invention is directed to a fastener for use in bone reparation. More particularly, the present invention is directed to a self-drilling, self-tapping screw used to reconnect bone fragments, with or without the use of a reinforcement plate.

BACKGROUND AND SUMMARY OF THE INVENTION

In repairing fractured bones, it is frequently necessary to reattach bone fragments using fasteners or a series of fasteners in conjunction with a plate. Many of the fasteners used in this application require a hole to be drilled before they can be installed. While this significantly reduces the torque the fastener experiences during insertion, clinical tests have shown that up to ⅓ of the fasteners inserted with this technique establish inadequate bone/screw contact to achieve adequate connection. Other fasteners are awkward, particularly in tight places associated with operating procedures, since they require two hands to install: one to hold the fastener and the other the driver. Further, a number of supposedly self-drilling, self-tapping fasteners lack adequate strength to sustain the torque required in this application.

The self-drilling, self-tapping screw of the present invention overcomes the defects of the prior art fasteners. Its self-drilling and self-tapping features allow installation without the need to pre-drill an aperture to receive it. The process of self-drilling and self-tapping provides increased surface contact between bone and screw thread improving the holding power of the screw. In addition, the screw of the present invention removes a minimal amount of bone material prior to thread engagement. The screw is made of a material which is capable of receiving high torque, preferably a material selected from the group consisting of titanium alloys, cobalt chrome and high strength resinous polymers.

The screw has three basic sections: a tip region, a body region and a head region. The tip region has a point with an included angle of between 45° and 50° and more preferably, between 46° and 49°, a compromise between penetrability and strength requirements. The tip region has a retention thread that extends substantially throughout its entire length. The body region has a substantially uniform diameter and a retention thread which also extends substantially throughout the entire length of the body region. The head region includes a head which has a drive recess and a portion underlying said head which is threadless.

The head region has been specifically designed to maximize drive torque to enable the screw to penetrate the hard cortical bone portion while minimizing the material removed from the head so as not to unduly weaken the integrity of the head. Removal of excess material can result in a weakened head region which can result in the head twisting off the body or the driver stripping the recess. The drive recess is cruciform in shape and extends from between 70 and 95% of the maximum diameter of the head to increase surface contact with the driver and, thereby, the torque transfer capability. Since the recess does not extend the full width, the outer periphery of the head maintains its integrity as a cylinder of metal which has significantly greater strength and resistance to stripping than it otherwise would have. The bottom of the recess is arcuate to minimize the amount of material removed from the head in forming the recess. The recess has retention means so said screw can be attached to a driver and inserted by a single hand of a user. The retention means preferably takes the form of an interference fit with the driver. A cutting flute extends from the tip region into the body region and removes bone fragments to permit penetration and thread formation by the screw in at least one of the bone sections which are being reattached by said screw.

A preferred but optional feature of the screw is that the head have an included angle δ of at least about 90° to prevent pull through of the screw while minimizing its profile. Additionally, it is a preferred feature the threads on both the tip region and body region have substantially similar shape and pitch, including that the lead angle of each be between 48° and 52° and the trailing angle be between 98° and 102° as measured from the centerline of the screw. More preferably, the retention thread of said tip region has a thread pitch which is slightly smaller than the thread pitch of said retention thread of said body region.

Various other features, advantages and characteristics of the present invention will become apparent to one of ordinary skill in the art after a reading of the following specification.

BRIEF DESCRIPTION OF THE DRAWINGS

The preferred embodiment(s) of the present invention is/are described in conjunction with the associated drawings in which like features are indicated with like reference numerals and in which FIG. 1 is a cross-sectional side view of a first embodiment of the self-drilling, self-tapping screw of the present invention;

FIG. 1A is a top view of the screw showing the drive recess;

FIG. 2 is a cross-sectional side view of a second embodiment of the screw of the present invention, the features being embodied in a shorter screw;

FIG. 3 is a side view of the driver used to provide torque to the cruciform slot in the self-drilling, self-tapping screw of the present invention;

FIG. 3A is a detailed side view of the tip of the driver; and

FIG. 3B is an end view of the tip shown in FIG. 3A.

DETAILED DESCRIPTION OF PREFERRED EMBODIMENT(S)

A first preferred embodiment of the self-drilling, self-tapping screw of the present invention is shown in FIG. 1 generally at 20. The screw 20 has three sections: a tip region 22, a body region 30 and a head region 40. Tip region 22 has a point 24 for penetrating the bone to initiate drilling. The included angle α for the tip region is preferably between 45° and 50° and more preferably between 46° and 49°. This angle proved to be the optimum compromise between strength and penetrability for this application. Retention thread 26 is formed over substantially the entire length of tip region 22. The overall length of the screw is typically between 4 and 14 mm; by extending the thread throughout the tip region, the amount of bone removed before thread engagement is minimized and the holding power of the thread is maximized.

Body region 30 has a uniform base diameter 32, and a retention thread 36 which extends substantially the entire length of the body region. The thread configuration and pitch of retention thread 36 on body region 30 is similar to that of retention thread 26 on tip region 22. Typically, it is desirable for the pitch of retention thread 26 to be slightly smaller than that of retention thread 36. The thread configuration will be substantially identical having a lead angle β of between 48° and 52° and a trailing angle γ of between 98° and 102°, each as measured from the centerline of the screw.

A cutting flute 38 extends over some portion of the length of screw 20. In this embodiment, flute 38 extends through portions of both the tip region 22 and the body region 30. Flute 38 cuts and removes bone fragments from the segments being repaired in order to permit threads to be formed therein in a manner well known in the self-tapping screw art. Flute 38 is preferably made by plunging a mill (not shown) into the tip region and removing material to generally about the centerline of the screw. This will form a flat cutting surface 39 which will engage the host bone as the screw is rotated in a clockwise direction into the bone. The configuration of the tip region 22 including the included angle α the threads extending to the very tip, and the position of the cutting flute 38 result in minimal amount of bone material being removed prior to thread engagement. This helps maximize the amount of bone in contact with the screw 20.

The head region 40 is generally threadless throughout its length and has a generally frusto-conical head 42 with an included angle δ of at least 90° to prevent pull through. It is generally not desirable, however, for the head 42 to have an inclusive 180° as in the case of some fasteners and to, thereby, overlie either the bone segment or the reinforcing plate. It is preferred that the angle δ not exceed about 120° to minimize its profile so the screw 20 may be, in effect, countersunk with head 42 having a rounded upper surface 44, which is less obtrusive. In fact, the radius of the upper surface 44 is preferably greater than the radius of the head 42 by a factor in the range of between 2 and 4. Head 42 has a cruciform drive slot 46 (FIG. 1A) which maximizes the torque that can be delivered to screw 20 during insertion. The bottom of the drive slot 46 is rounded to minimize the amount of material removed from the head 42 in creation of the slot to maximize the strength of the head 42.

It is preferred that the orthogonal slots forming drive slot 46 extend outwardly from between 70% and 95% of the maximum diameter of head 42. In this way, drive slot 46 extends far enough outwardly to provide adequate drive torque while not weakening the integrity of the head 46 (as a slot that extended completely across the head would). Slots that extend the full width frequently experience stripping or twisting off of the head 42 from the body 30 as a result of too much material being removed in slot formation. Head region 40 includes an unthreaded portion 48 that underlies head 42 and generally has the same diameter as the height of thread 36. The screw 20 is preferably made of one of a materials selected from the group consisting of a titanium alloy, cobalt chrome and a high-strength resinous polymer. This choice of material helps provide the strength required to withstand the drive torque screw 20 will experience during insertion.

A second shorter embodiment of the self-drilling, self-tapping screw of the present invention is shown in FIG. 2 generally at 20a. The screw 20a has the same three sections as the first embodiment: tip region 22a, body region 30a, and head region 40a. The body portion 30a is simply much shorter than in the first embodiment. This shorter screw 20a is shown to demonstrate that the principles of the present invention can be accomplished in screws of any length. The shorter screw 20a will be used for repairing bones having smaller diameters and for attaching reinforcement plates to the proximate surface of the hard cortical bone (not shown).

The driver 50 is shown if FIGS. 3, 3A and 3B. The thickness of each of the four arms 54 on cruciform tip 52 tapers outwardly slightly as it extends away from the tip so as to provide an interference fit with the cruciform slot 46 of the screws. This permits the screw 22 to be placed on tip 52 and driver 50 can be manipulated by one hand for placement. A pair of flats 56 (one shown) provide means to engage the rounded surfaces of handle portion 58 and provide torque. A grippable handle (not shown) could be cast over the handle portion 58 or handle 58 could be chucked in a drill, or other rotary power tool to effect installation.

The self-drilling, self-tapping fastener 20, 20a of the present invention provide a convenient alternative to the currently available fasteners. The high strength material used and the particular tip, thread and head configurations, enable the fastener 20, 20a to withstand the drive torques to which it is exposed without stripping the drive slot or twisting the head off the body. The use of a self-drilling, self-tapping fastener is not only a convenience to its user. Clinical tests have demonstrated that it provides superior bone/thread engagement and, therefore, better fastening. The use of an interference fit, or other suitable retention means, enable one-handed manipulation of the tool to effect insertion of the fastener.

Various changes, alternatives and modifications will become apparent to one of ordinary skill in the art following a reading of the foregoing specification. It is intended that any such changes, alternatives and modifications as fall within the scope of the appended claims be considered part of the present invention.

We claim:

1. A self-drilling, self-tapping screw used in repairing broken bones by reattaching at least a first and a second bone section, said screw having an overall length and comprising:

a tip region for penetrating the bone sections and initiating thread formation therein, said tip region having a point with an included angle of between about 45° and about 50° to provide a necessary strength and, yet, penetrate the bone, said tip region having a retention thread formed through substantially its entire length;

b) a body region having a substantially uniform diameter and having a retention thread formed substantially throughout its entire length;

c) a round head region including
   i) a head which has a maximum diameter and a drive recess, and
   ii) a portion underlying said head which is without any thread, said drive recess being cruciform in shape, said cruciform being formed by two ortho-gonal slots which each extend from between 70% and 95% of said maximum diameter to provide a required level of torque, said drive recess having retention means so said screw can be attached to a driver and inserted by a single hand of a user;

d) a cutting flute extending over at least a portion of said overall length for cutting and removing bone fragments to permit penetration and thread formation by said screw in at least one of said bone sections which are being reattached by said screw;

whereby a configuration of said head region including said drive recess provides said adequate level of torque required to permit said screw to be driven into said bone and adequate strength to resist deformation and twisting of said head off said body region of said screw during installation.

2. The self-drilling, self-tapping screw of claim 1 wherein said head of the head region has an included angle of at least about 90° to prevent pull through.

3. The self-drilling, self-tapping screw of claim 2 wherein the included angle of said head falls in the range of between about 90° and about 120°.

4. The self-drilling, self-tapping screw of claim 3 wherein a bottom portion of each said orthogonal slot is arcuate.

5. The self-drilling, self-tapping screw of claim 4 wherein a radius of an arc defining said arcuate bottom is approximately equal to said maximum radius of said screw head.

6. The self-drilling, self-tapping screw of claim 5 wherein an upper face of said screw head has an arcuate configuration, a radius of arc defining said arcuate configuration of said upper face being in a range of between two and four times said maximum radius of said screw head.

7. The self-drilling, self-tapping screw of claim 1 wherein said included angle of said tip is between 46° and 49°.

8. The self-drilling, self-tapping screw of claim 1 wherein said retention thread of said tip region and said body region have substantially similar shapes and pitches, including a lead angle of between 48° and 52° as measured from a centerline of said screw and a trail angle of between 98° and 102° as measured from said centerline.

9. The self-drilling, self-tapping screw of claim 1 wherein said retention means comprises an interference fit between said cruciform drive slot and the driver.

10. The self-drilling, self-tapping screw of claim 1 wherein said screw is comprised of a material capable of receiving high torque.

11. The self-drilling, self-tapping screw of claim 10 wherein said screw is made of a medical grade, biocompatible material.

12. The self-drilling, self-tapping screw of claim 11 wherein said screw is manufactured from a group of materials consisting of a titanium alloy, cobalt chrome and a high-strength resinous polymer.

13. A self-drilling, self-tapping screw used in repairing broken bones by reattaching at least a first and a second bone section, said screw having an overall length and comprising:
  a) a tip region for penetrating the bone sections and initiating thread formation therein:
  said tip region having a point with an included angle of between about 45° and about 50° to provide a necessary strength and, yet, penetrate the bone, said tip region having a retention thread formed through substantially its entire length;
  b) a body region having a substantially uniform diameter and having a retention thread formed substantially throughout its entire length said retention thread of said tip region has a thread pitch which is slightly smaller than the thread pitch of said retention thread of said body region;
  c) a round head region including
    i) a head which has a maximum diameter and a drive recess and
    ii) a portion underlying said head which is without any thread, said drive recess being cruciform in shape said cruciform being formed by two orthogonal slots which each extend from between 70% and 95% of said maximum diameter to provide a required level of torque, said drive recess having retention means so said screw can be attached to a driver and inserted by a single hand of a user;
  d) a cutting flute extending over at least a portion of said overall length for cutting and removing bone fragments to permit penetration and thread formation by said screw in at least one of said bone sections which are being reattached by said screw;
whereby a configuration of said head region including said drive recess provides said adequate level of torque required to permit said screw to be driven into said bone and adequate strength to resist deformation and twisting of said head off said body region of said screw during installation.

14. A head region for a self-drilling, self-tapping screw to be used in fractured bone reparation, said head region comprising
  i) a frusto-conical head which has a maximum diameter and a drive recess, and
  ii) a portion underlying said head which is without any thread, said frusto-conical head having an included angle of between about 90° and about 120°,said drive recess being cruciform in shape, said cruciform being formed by two orthogonal slots which each extend from between 70% and 95% of said maximum diameter to provide a required level of torque, said drive recess having retention means so said screw can be attached to a driver and inserted by a single hand of a user, each of said orthogonal slots being arcuate on its bottom to effect minimum removal of material from said head while providing maximum surface engagement with a driver received in said drive recess, a radius of an arc defining said arcuate bottom being proximate a maximum radius of said screw head, an upper face of said screw head having an arcuate configuration, a radius of arc defining said arcuate configuration of said upper face being in a range of between two and four times said maximum radius of said screw head;
whereby a configuration of said head region including said drive recess provides said adequate level of torque required to permit the screw to be driven into said bone and adequate strength to resist both deformation of said drive recess and said head being twisted off a body region of the screw during installation.

\* \* \* \* \*